United States Patent [19]

Ko et al.

[11] 4,249,527

[45] Feb. 10, 1981

[54] CONTINUOUS POSITIVE AIRWAY PRESSURE ADMINISTRATING APPARATUS

[75] Inventors: Wen H. Ko; David G. Fleming, both of Cleveland Hts.; Harry J. Derda, Beachwood; William O. Martin, Chesterland, both of Ohio

[73] Assignee: Case Western Reserve University, Cleveland, Ohio

[21] Appl. No.: 10,735

[22] Filed: Feb. 9, 1979

Related U.S. Application Data

[63] Continuation of Ser. No. 782,222, Mar. 28, 1977, abandoned.

[51] Int. Cl.³ ............................................. A61M 16/00
[52] U.S. Cl. ................................ 128/204.18; 128/911; 128/205.17; 128/205.24; 128/206.22
[58] Field of Search ...................... 128/204.18, 205.12, 128/205.13, 205.17, 205.19, 205.25, 205.18, 207.14, 207.15, 207.16, 200.24, 206.22

[56] References Cited

U.S. PATENT DOCUMENTS

| 2,012,441 | 8/1935 | Willston et al. | 128/205.25 |
|---|---|---|---|
| 2,248,477 | 7/1941 | Lombard | 128/205.25 |
| 2,371,965 | 3/1945 | Lehmberg | 128/205.25 |
| 3,856,051 | 12/1974 | Bain | 128/204.18 |
| 4,007,737 | 2/1977 | Paluch | 128/188 |

FOREIGN PATENT DOCUMENTS

| 93941 | 8/1923 | Austria | 128/205.12 |
|---|---|---|---|
| 1491776 | 5/1969 | Fed. Rep. of Germany | 128/205.18 |
| 520342 | 2/1921 | France | 128/205.12 |

*Primary Examiner*—Henry J. Recla
*Attorney, Agent, or Firm*—Paul L. Gardner

[57] ABSTRACT

An apparatus for delivering continuous positive airway pressure to a patient (e.g., an infant) includes a cradle assembly for firmly and adjustably supporting the head of a patient to whom continuous positive airway pressure is to be delivered, a support frame assembly mounted on the cradle assembly for adjustably supporting a disposable airway set, and a disposable airway set which receives fresh air and delivers it, under pressure, to a patient. The cradle assembly includes a head-supporting cradle which may be moved to any one of a number of angular positions. A pair of adjustable head-restraining plates are mounted in the cradle for firmly supporting heads of different sizes. The support frame assembly which receives and holds the disposable airway set is mounted on one end of the head-supporting cradle and can be adjusted relative to the cradle for accurate positioning of a nasal cannula at the delivery end of the disposable airway set. The support frame assembly includes a swingable support arm which receives and retains the disposable airway set. The swingable support arm may be swung to a position wherein the disposable airway set retained therein may be swung out of the vicinity of the patient's head to facilitate insertion and removal of the patient's head and treating of the patient. The disposable airway set includes a pop-off valve assembly for limiting the maximum amount of pressure of the air delivered to the patient and a pressure control valve for controlling the pressure of the air delivered to the patient. The disposable airway set is comprised of two airway arms which are connected to one another by a connector member which establishes fluid communication between the two arms. One end of one of the airway arms of the disposable airway set receives fresh air from an air supply, and the other end of the first arm has a re-breather bag connected thereto for "bagging" the patient. One end of the second airway arm is provided with a nasal cannula for attachement to the patient, and the other end of the second arm is provided with the pressure control valve. The disposable airway set is adapted to be used for one patient only, and discarded after use.

10 Claims, 16 Drawing Figures

CONTINUOUS POSITIVE AIRWAY PRESSURE ADMINISTRATING APPARATUS

This is a continuation of application Ser. No. 782,222, filed Mar. 28, 1977, now abandoned.

FIELD OF THE INVENTION

The present invention relates to respirator devices, and more particularly to an improved apparatus for delivering continuous positive airway pressure to a person (e.g., an infant) suffering from respiratory distress syndrome.

BACKGROUND OF THE INVENTION

Idiopathic respiratory-distress syndrome has been reported to be the leading cause of respiratory failure in newborn infants. Infants afflicted with this syndrome experience substantial difficulty in breathing because the alveous of their lungs are unable to sustain inflation.

In an effort to assist infants afflicted with idiopathic respiratory-distress syndrome, it has been proposed that continuous positive airway pressure be administered to such patients. See, for example, an article entitled "Treatment of the Idiopathic Respiratory-Distress Syndrome with Continuous Positive Airway Pressure" by Gregory et al., published in the June 17, 1971 issue of the New England Journal of Medicine (Volume 284, No. 24).

While various types of continuous positive airway pressure administration apparatuses have been proposed and used (see, for example, U.S. Pat. Nos. 3,786,809; 3,827,433 and 3,842,828), none has proven to be entirely satisfactory. The prior art apparatuses for delivering continuous positive airway pressure to infants have been relatively complex in structure and design, have not been entirely reliable in use and/or require relatively expensive sterilization procedures following use by each patient. Another problem associated with the prior art apparatuses for administrating continuous positive airway pressure to patients is that such apparatuses have failed to provide means for minimizing rebreathing by the patient of exhaled or exhausted air.

OBJECTS AND SUMMARY OF THE INVENTION

In view of the foregoing, it is an object of the present invention to provide an improved apparatus for administering continuous positive airway pressure to patients, such as newborn infants suffering from idiopathic respiratory-distress syndrome, which is simpler and less expensive than the prior art apparatuses have been.

It is a further object of the present invention to provide a continuous positive airway pressure administration apparatus which is sturdy, reliable and efficient in use.

Another object of the present invention is to provide a simple, sturdy, reliable and efficient continuous positive airway pressure administration apparatus which is less expensive to manufacture than prior art apparatuses have been.

Still another object of the present invention is the provision of a sterile apparatus for administering continuous positive airway pressure which does not require sterilization of the apparatus after each use.

Another object of the present invention is the provision of a continuous positive airway pressure administration apparatus which is equipped with controls to assure that the air being delivered to the patient is at the proper, desired pressure.

Another object of the present invention is the provision of a continuous positive airway pressure administration apparatus which minimizes re-breathing by the patient of exhausted or exhaled air.

A further object of the present invention is the provision of a continuous positive airway pressure administration apparatus which has a disposable airway set to avoid the necessity for expensive and time consuming sterilization of the apparatus.

Other objects and the numerous attendant advantages of the present invention will become apparent from the following description of one preferred embodiment thereof.

DETAILED DESCRIPTION OF A PREFERRED EMBODIMENT

FIGS. 1-15 of the drawings illustrate one preferred embodiment of the continuous positive airway pressure (CPAP) administration apparatus 20 constructed in accordance with the teachings of the present invention.

Figure 1:
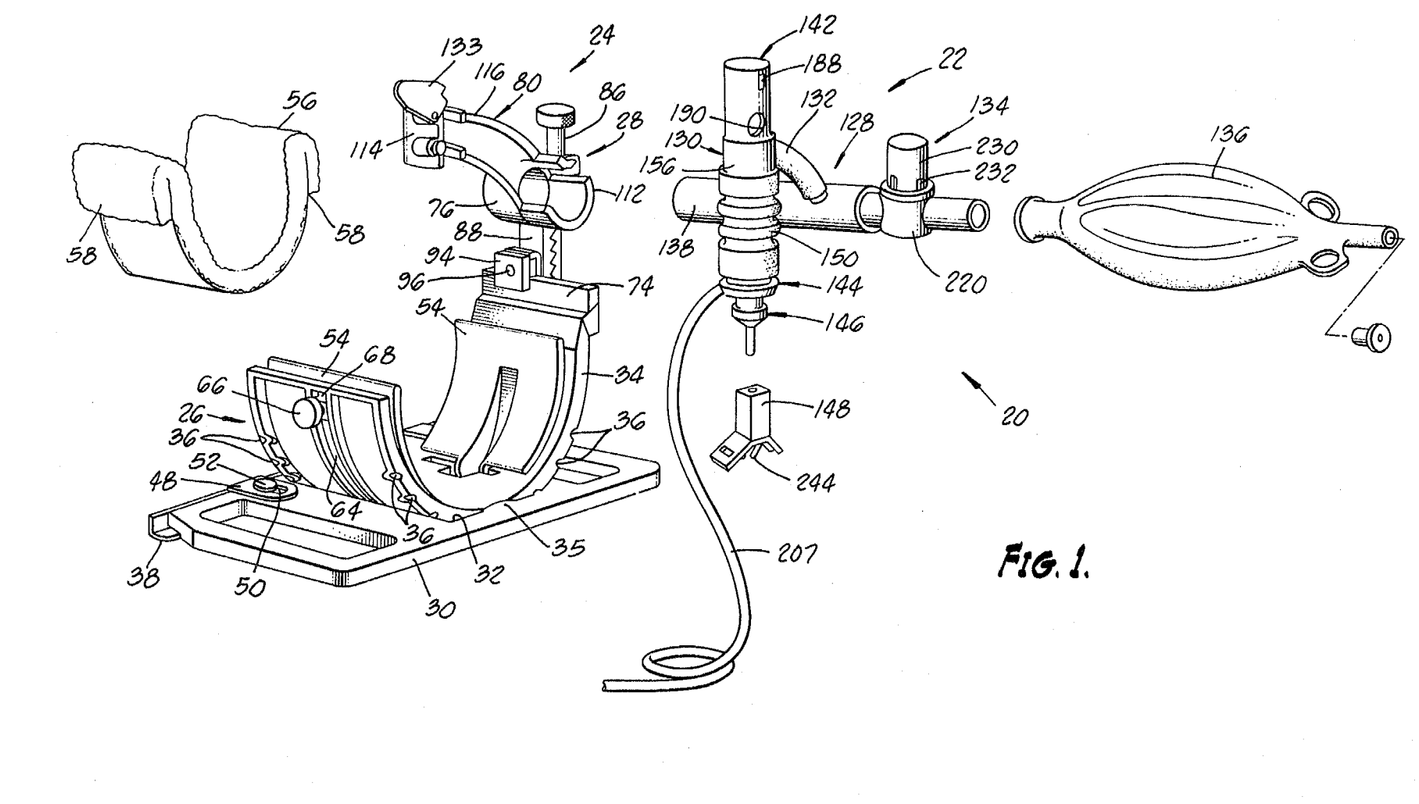
FIG. 1 is an exploded, perspective view of a continuous positive airway pressure administration apparatus constructed in accordance with the teachings of the present invention.

As best shown in FIG. 1, the continuous positive airway pressure administration apparatus 20 of the present invention includes a cradle assembly 26 for firmly and adjustably holding the head of a patient, a support frame assembly 24 mounted on the cradle assembly, and a disposable airway set 22 received and held by the support frame assembly.

The support frame assembly 24 includes a support set 28 which is adjustably mounted on one end of a cradle 34 which forms part of the cradle assembly 26, and a support arm 80 which receives and holds the disposable airway set 22.

The cradle assembly 26 is best illustrated in FIGS. 1, 1A, 2 and 3. It includes a base member 30 having an arcuate groove 32 therein for detachably receiving a generally semi-cylindrical head support cradle 34. Two inwardly projecting ledges 35, 35 (FIG. 1A) on the base member 30 overlie the sides of the arcuate groove 32 to retain the cradle 34 and prevent it from being lifted out of the groove. The cradle 34 must be rotated approximately 90 degrees to remove it from the base member 30.

Figure 1A:
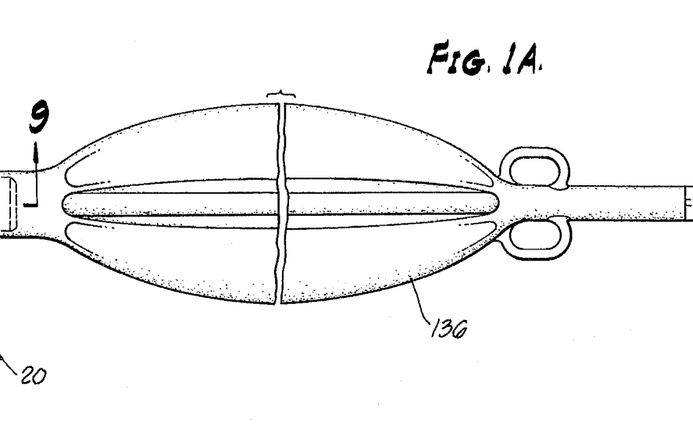
FIG. 1A is a top plan view of a continuous positive airway pressure administration apparatus shown in FIG. 1, showing the apparatus is assembled condition.
Figure 4:
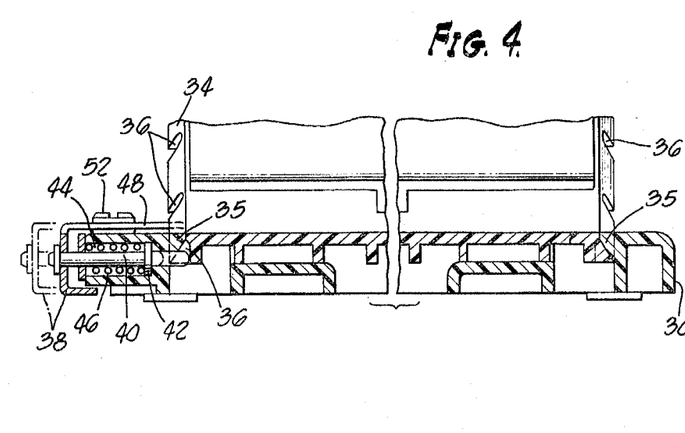
FIG. 4 is a side, sectional elevation view taken along the plane 4—4 of FIG. 1A and looking in the direction of the arrows, showing the manner in which the head support cradle of the apparatus is connected to the base.
Figure 5:
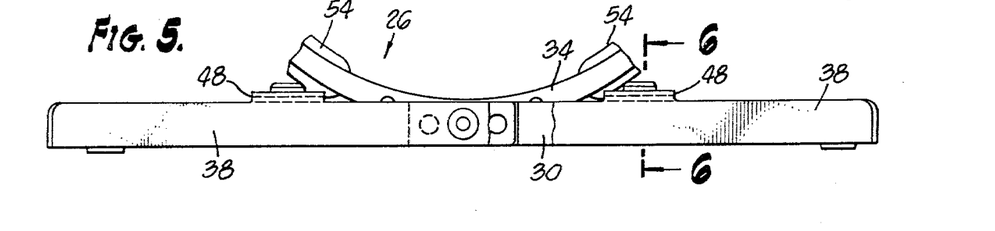
FIG. 5 is an end elevation view taken along the plane 5—5 of FIG. 2 and looking in the direction of the arrows, further showing the interconnecting relationship between the head support cradle and the base.

The manner in which the head support cradle 34 is rotatably and detachably secured to the base member 30 is best illustrated in FIGS. 4 and 5. The cradle has a plurality of spaced slots 36 in each of its semi-circular side edges and the base member 30 is provided with a cradle release lever 38 (see FIG. 1A, as well as FIGS. 4 and 5) which carries a spring-loaded pin 40. As shown in FIGS. 1A and 4, the pin 40 has an annular seat 42 thereon which is disposed in a spring chamber 44 in one side of the base member 30 (FIG. 4), and a compression spring 46 is disposed in the spring chamber for normally urging the end of pin 40 into one of the slots 36 in one of the semi-circular side edges of the cradle 34. As shwn in FIG. 4, when it is desired to rotate the cradle 34 in either a clockwise or counterclockwise direction (to tilt the patient's head in one direction or the other) the cradle release lever 38 is pulled outwardly to retract the pin 40, against the force of the compression spring 46 to the position shown in phantom lines in FIG. 4. With the pin 40 so retracted, the cradle 34 may be rotated in either a clockwise or counterclockwise direction to tilt the patient's head to the desired angular position. When the desired position has been reached, the cradle release lever 34 is released to allow the compression spring 46 to force the pin 40 inwardly to the position shown in FIG. 4 wherein the inner end of the pin 40 engages in one of the slots 36 in the side edge of the cradle 34 to retain the cradle in the angular position which has been selected.

As noted above, the support frame assembly 24 which supports the disposable airway set 22 is mounted on one end of the cradle 34. The construction details showing how the support frame assembly is adjustably mounted on the cradle will be described below. However, it should be noted that the head support cradle 34 can be rotated until it is entirely out of the arcuate groove 32, whereupon the cradle may be turned 180° and reinserted in the arcuate groove 32 in the base member 30. This permits the disposable airway set 22 and the support frame assembly 24 to be positioned on either the right side or the left side of the patient.

Figures 2, 6:
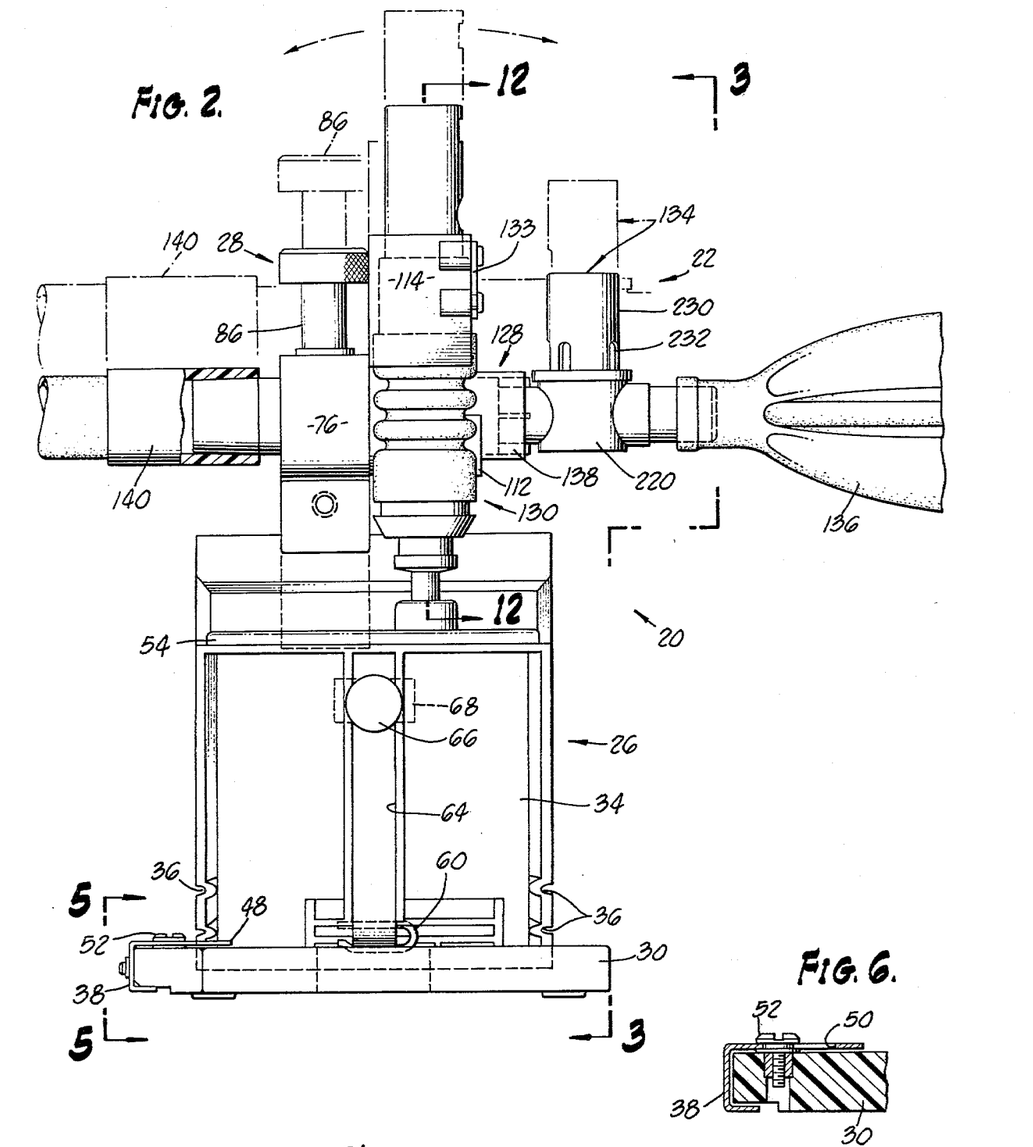
FIG. 2 is a side elevation view, partly in section, of the continuous positive airway pressure (CPAP) administration apparatus shown in FIG. 1A, and looking in the direction of the arrows 2—2 in FIG. 1A.
FIG. 6 is a sectional side elevation view taken along the plane 6—6 of FIG. 5, showing the manner in which the cradle release lever is connected to the base of the apparatus.

The structure of the cradle release level 38 is best shown in FIGS. 1A, 4 and 6. The lever 38 extends along one side (the left side, as viewed in FIGS. 1A, 4 and 6) of the base member 30. The lever 38 is generally in the shape of a right angle, having one side adapted to lie along one side surface of the base member 30, and the other side adapted to lie along the bottom surface of the base member. As shown in FIGS. 1A, 4 and 6, the lever 38 includes a pair of inwardly extending tabs 48, 48, each of which is provided with an elongated slot 50 in approximately the center thereof. As shown in FIG. 6, the slot 50 is adapted to receive a screw 52 which extends downwardly into the base member 30 from the top surface thereof. By virtue of this construction, the cradle release lever 38 may be moved outwardly a distance corresponding to the length of the longitudinal slots 50, 50 in the inwardly extending tabs 48, 48, from the position shown in solid lines in FIG. 4 to the position shown in phantom lines.

When it is desired to release the cradle 34 for rotation or removal from the base member 30, one end or the other of the cradle release lever 38 is moved to the left, as shown in FIGS. 1A and 4 so that the pin 40 will move to the left to the phantom line position shown in FIG. 4, thereby permitting rotation or removal of the cradle member. When the cradle release lever 38 is released, the compression spring 46 will force the pin 40 to its solid line position shown in FIG. 4, wherein the end thereof extends into one of the slots 36 in the side of the cradle to again lock the cradle in place.

Figure 3:
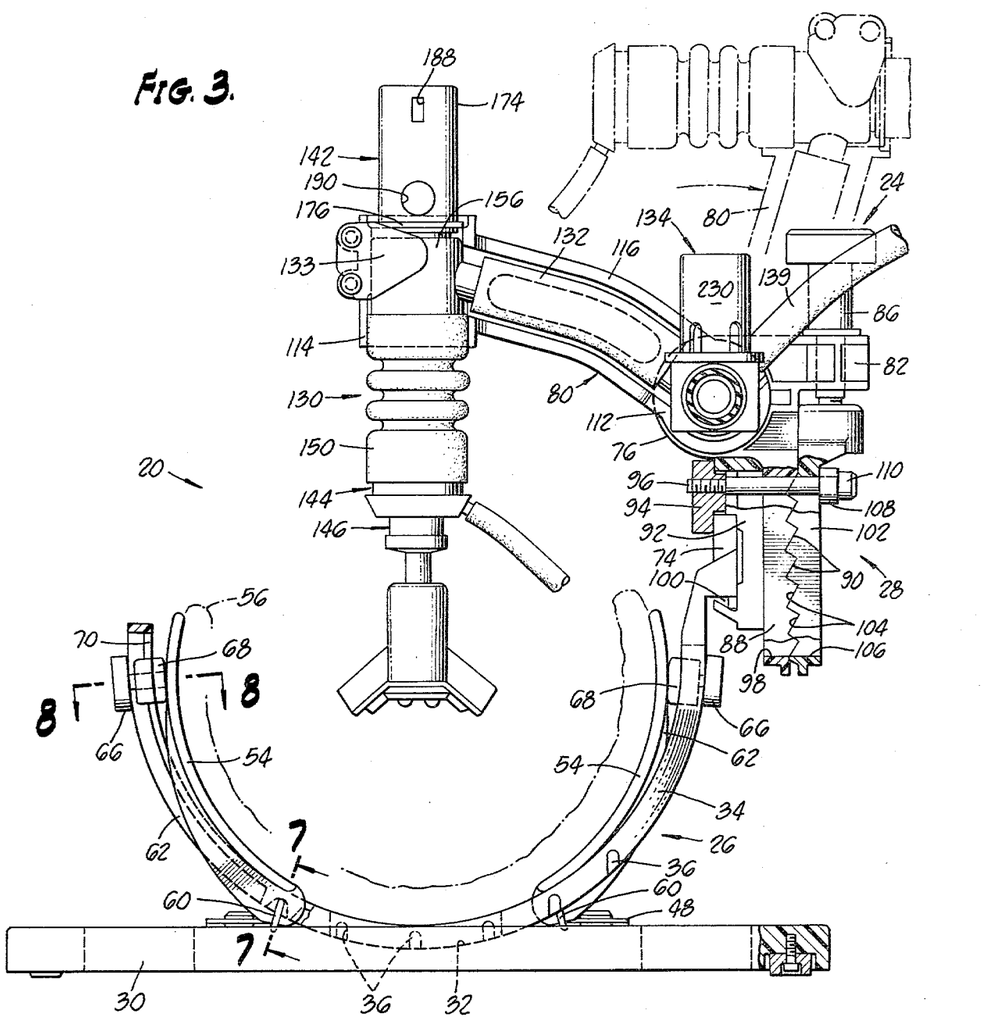
FIG. 3 is an end view of the CPAP administration apparatus shown in FIGS. 1A and 2, and looking in the direction of the arrows 3—3 in FIG. 2.

As best shown in FIGS. 1 and 3, a pair of generally arcuate head restraining plates 54, 54 are pivotably mounted on the inner arcuate surfaces of the semi-cylindrical cradle 34. The purpose of these plates is to firmly, but gently, grasp the head of the patient.

A pad 56 of a suitable soft material (i.e., lamb's wool) is provided for lining the interior of the arcuate restraining plates 54, 54. As shown in FIG. 1, the pad is provided with a pocket 58 on either end thereof for slipping over the upper ends of the arcuate restraining plates 54, 54.

Figure 7:
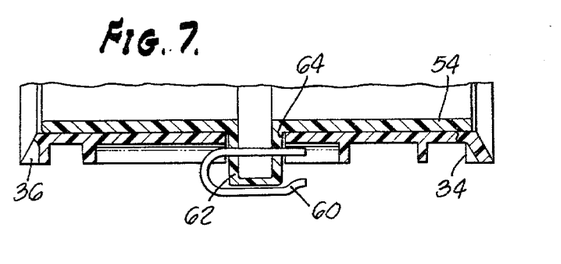
FIG. 7 is a section side elevation view taken along the plane 7—7 of FIG. 3 and looking in the direction of the arrows, showing the manner in which each head restraining plate of the cradle assembly is pivotably connected to the head support cradle.

Each of the arcuate restraining plates 54 is pivotably mounted within the inner arcuate surface of the cradle by means of a generally C-shaped restraining pin 60. As best shown in FIG. 7, each of the pins 60 extends through a grooved ramp 62 in its restraining plate 54, beyond the outer surface of the cradle 34. Each of the C-shaped restraining pins 60 biases its associated head restraining plate 54 toward the inner surface of the cradle 34. In other words, looking at FIG. 3, the left-hand restraining plate 54 is biased in a counterclockwise direction and the right-hand restraining plate 54 is biased in a clockwise direction, both being biased radially outwardly.

Figure 8:
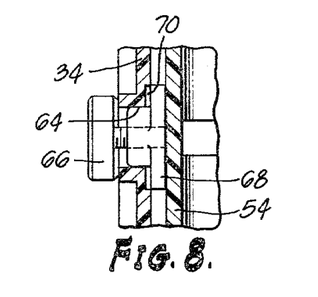
FIG. 8 is a sectional plan view taken along the plane 8—8 of FIG. 3 and looking in the direction of the arrows, showing the manner in which the adjustment knob for each of the head restraining plates in the cradle assembly is connected to the head support cradle for adjusting the position of the head restraining plates.

When a patient's head is inserted into the cradle assembly 26, the head restraining plates 54, 54 are adapted to be moved radially inwardly to firmly, but gently, grasp the patient's head. For this purpose, each end of the cradle 34 is provided with a longitudinally extending slot 64 (see FIG. 2), through which extends an adjustment knob 66 having a slide member 68 secured on the end thereof. Each of the slides 68 cooperates with the grooved ramp 62 provided on the outer side of each of the restraining plates. The relationship of the adjustment knob 66 and slide 68 for each of the restraining plates 54 is shown in FIG. 8. Each of the adjustment knobs 66 extends through the outer surface of its respective arcuate end of the cradle and terminates with the slide member 68 which is generally rectangular and disposed in a rectangular groove 70 in the inner surface of the cradle. (See FIGS. 2 and 8.) As the adjustment knob 66 and slide 68 are moved downwardly, the slide 68 will engage the ramp 62 on the outer surface of the restraining plate 54 to cam the restraining plate radially inwardly, against the patient's head. The soft pad will conform to the patient's head and soften the restraining force exerted by the restraining plates 54, 54.

Referring to FIGS. 1 and 3, the support set 28 of the support frame assembly 24 is mounted on a track 74 provided on the upper right-hand end (as viewed in FIG. 3) of the cradle 34.

Figures 9, 10, 11:
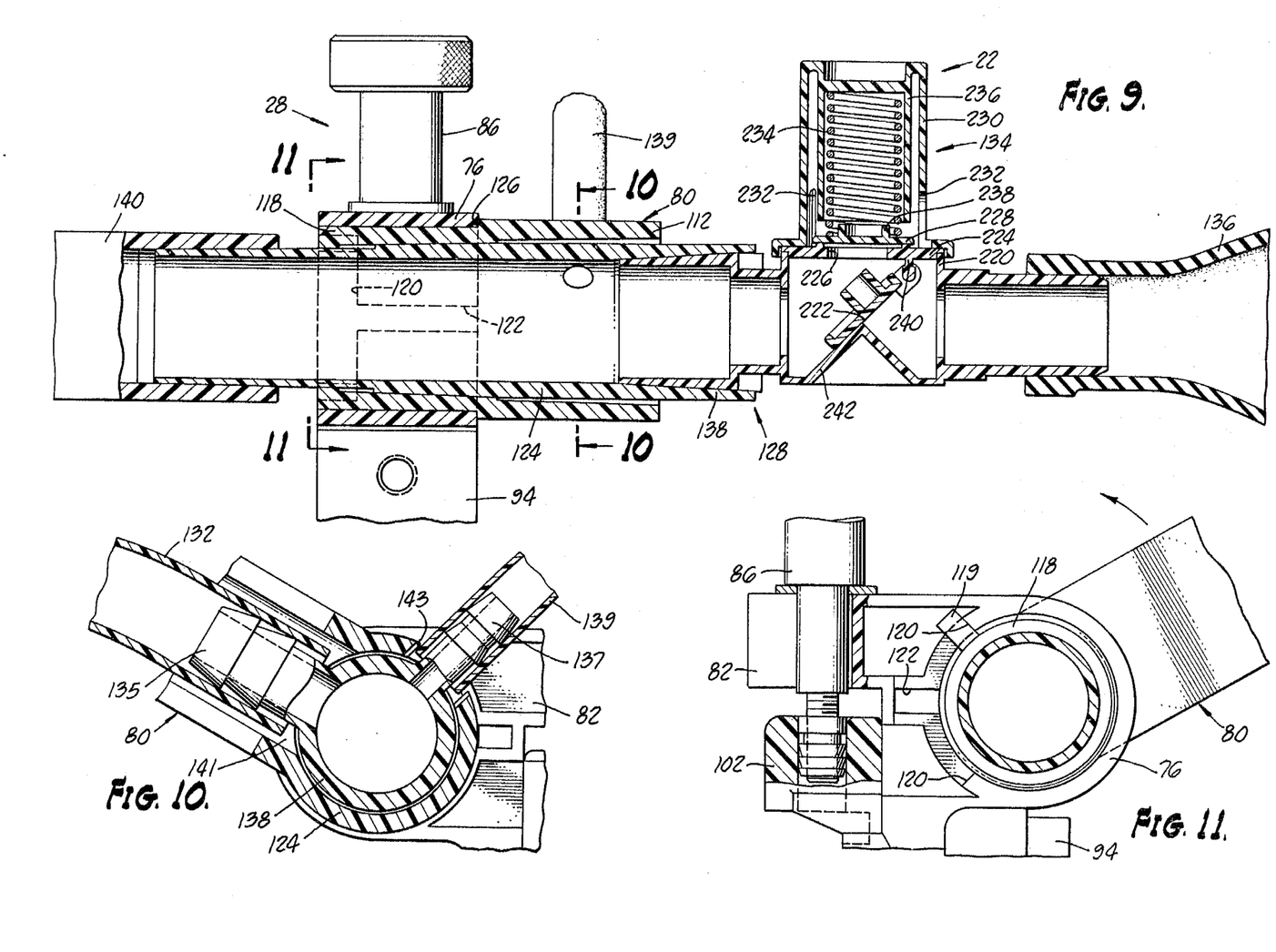
FIG. 9 is a sectional side elevation view taken along the plane 9—9 of FIG. 1A and looking in the direction of the arrows, showing one arm of the disposable airway set of the CPAP administration apparatus of the present invention.
FIGS. 10 and 11 are section end elevation views taken along the planes 10—10 and 11—11, respectively, of FIG. 9 and looking in the direction of the arrows, showing the manner in which the horizontal arm of the disposable airway set of the CPAP administration apparatus of the present invention is received in and supported by the support frame assembly for the disposable airway set.

As best shown in FIGS. 3 and 9, the adjustable support set 28 includes a generally horizontally extending cylindrical holder 76 which retains the support arm 80. The support set 28 further includes an outwardly extending flange 82 (extending to the right, as shown in FIG. 3) which has a vertical opening therein for receiving an adjustment screw 86, and a downwardly extending flange 88 having cam surfaces 90 thereon arranged in a step-like fashion. The support set 28 is supported on the upper right end (as viewed in FIG. 3) of the head support cradle 34 by means of a pair of clamping members 92 and 94 and a locking bolt 96 which extends through a vertically extending slot 98 in the downwardly extending flange 88. The clamping member 92 has a groove 100 therein which receives the horizontally extending track on the upper right end (as viewed in FIG. 3) of the head support cradle.

The locking bolt 96 also extends through a wedge member 102 having cam surfaces 104 thereon arranged in step-like fashion to mate with the cam surfaces 90 on the downwardly extending flange 88 of the support set 28. The wedge member 102 has a vertically extending slot 106 therein which aligns with slot 98 in the flange 88 and through which the locking bolt 96 extends. The wedge member 102 is sandwiched between the flange 88 and an annular washer 108 adjacent the head 110 of the locking bolt 96.

From the foregoing, it will be appreciated that when the locking bolt 96 is tightened to draw the clamping member 94 against the clamping member 92 having the track-receiving groove 100 therein, the mating clamping members 92 and 94 will grip the upper end of the track 74.

As shown in FIG. 3, the lower end of the adjustment screw 86 is threaded and screws into a threaded opening in the upper end of the wedge member 102. Assuming that the threads on the lower end of the adjustment screw 86 are right-hand threads, as the adjustment knob is rotated in a clockwise direction (as viewed in FIG. 1A), the threaded end of the adjustment screw will turn in the threaded hole in the upper end of the wedge member 102 to draw the wedge member upwardly (as viewed in FIG. 3) relative to the downwardly extending flange 88 of the support set 28. As the wedge member 102 is drawn upwardly, its cam surfaces 104 will rise along the cam surfaces 90 on the flange 88 to cam the wedge member and the flange 88 apart, to tighten the adjustable support set 28 in place.

When the adjustment screw 86 is rotated in a counterclockwise direction, as viewed in FIG. 1A, the threaded bottom end of the adjustment screw will turn in a counterclockwise direction in the threaded hole in the upper end of the wedge member 102 (again, assuming the threads are right-hand threads) to move the wedge member 102 and the flange 88 toward one another, i.e., toward the position shown in FIG. 3. When so positioned, the clamping members 92 and 94 will only loosely receive the horizontally extending track 74 on the upper right-hand end of the head support cradle (as viewed in FIG. 3) so that the entire support set 28 may be moved laterally (i.e., to the right and left, as viewed in FIGS. 1A and 2) to laterally position the support set 28 in the desired place on the head support cradle 34. Further, the entire support set 28 can be raised and lowered by virtue of the vertically extending slots 106, 98 in the wedge member 102 and the downwardly extending flange 88, respectively. When the desired lateral and vertical positions of the support set 28 have been selected, the adjustment screw 86 is rotated in a clockwise direction to raise the wedge member 102 and cam the wedge member and flange 88 apart and firmly clamp the support set 28 in place.

The support arm 80 of the support frame assembly 24 is retained by support set 28 and holds the disposable airway set 22. The support arm 80 incudes a horizontally extending cylindrical portion 112 (best shown in FIG. 9) for receiving one arm of the disposable airway set 22, and a vertically extending semi-cylindrical portion 114 (best shown in FIG. 3) for receiving and holding the other arm of the disposable airway set 22. The horizontally and vertically extending portions 112 and 114 of the support arm 80 are integrally connected by a slightly curved, semicylindrical connecting portion 116 (see FIGS. 1 and 3).

As best shown in FIG. 9, the horizontally extending cylindrical portion 112 of the support arm 80 includes a forward section 118 which extends into the cylindrical holder 76 of the support set 28 and is retained thereby. As shown in phantom lines in FIG. 1A and in solid lines in FIG. 11, the forward section 118 of the horizontally extending cylindrical portion 112 of the support arm 80 has a radially-outwardly extending key member 119 thereon which extends into an arcuate slot 120 in the forward end (left end as viewed in FIG. 9) of the cylindrical holder 76 of the support arm 80. As best shown in FIGS. 9 and 11, the arcuate slot 120 in which the key 119 rides is approximately 90° in circumferential length.

As shown in FIGS. 9 and 11, the cylindrical holder 76 of the support set 28 is provided with a horizontally extending slot 122 which receives the key member 119 when the forward end 118 of the horizontally extending portion 112 of the support arm 80 is inserted through the cylindrical holder 76. The key 119 which rides in the arcuate slot 120 prevents the horizontally extending portion 112 of the support arm 80 from moving to the right (as viewed in FIGS. 1A, 2 and 9) and out of the cylindrical holder 76.

As shown in FIG. 9, the rear section (i.e., the right end as viewed in FIG. 9) of the horizontally extending cylindrical portion 112 of the support arm 80 has a slightly enlarged out diameter forming a circumferential shoulder 126 which limits movement of the support arm to the left. Thus, the key member 119 and the circumferential shoulder 126 on the horizontally extending cylindrical portion 112 of the support arm 80 cooperate to maintain the support arm in place in the support set 28.

As shown in FIG. 3, the support arm may be raised 90° from the position shown in solid lines in FIG. 3 to the position shown in phantom lines in FIG. 3. The rotation of the support arm 80 is limited to 90° by the size of the arcuate slot 120 (FIGS. 9 and 11) in the cylindrical holder 76 in which the key 119 rides.

As best shown in FIG. 1, the disposable airway set 22 which is retained by the support arm 80 includes a generally horizontally extending arm 128 and a generally vertical extending arm 130 which communicate with one another through a connecting hose 132. The horizontally extending arm 128 is received in and held by the horizontally extending cylindrical portion 112 of the support arm 80, while the vertically extending arm 130 is received in and held by the vertically extending semi-cylindrical portion 114 of the support arm. As shown in FIGS. 1 and 3, a pivotably mounted gate 133 is provided on the semi-cylindrical vertical portion 114 of the support arm 80 for holding the vertical arm 130 of the disposable airway set 22 in place.

Referring to FIG. 9, the horizontally extending arm 128 of the disposable airway set 22 includes a pop-off valve assembly 134 which has one end (the right end, as viewed in FIG. 9) connected to a rebreather bag 136, and the other end (the left end as viewed in FIG. 9) connected to a cross-connector tube 138. The other end of the cross-connector tube 138 is connected to the end of an air supply hose 140.

As best shown in FIG. 10, the cross-connector tube 138 of the horizontal arm 128 of the disposable airway set 22 is provided with two circumferentially-spaced nozzles 135 and 137. The nozzle 135 is connected to one end of the connecting hose 132 for establishing fluid communication between the horizontal and vertical arms 128 and 130, respectively, of the disposable airway set 22. The nozzle 137 is connected to a tube 139 which may be connected to a suitable pressure monitoring device (not shown) for permitting monitoring of the pressure of the air delivered to the patient by the apparatus 20 of this invention.

As shown in FIG. 10, the rear cylindrical section 124 of the horizontal portion 112 of the support arm 80 is provided with circumferentially-spaced, radial openings 141 and 143 for receiving and accommodating the nozzles 135 and 137, respectively.

Figures 12, 13, 14, 15:
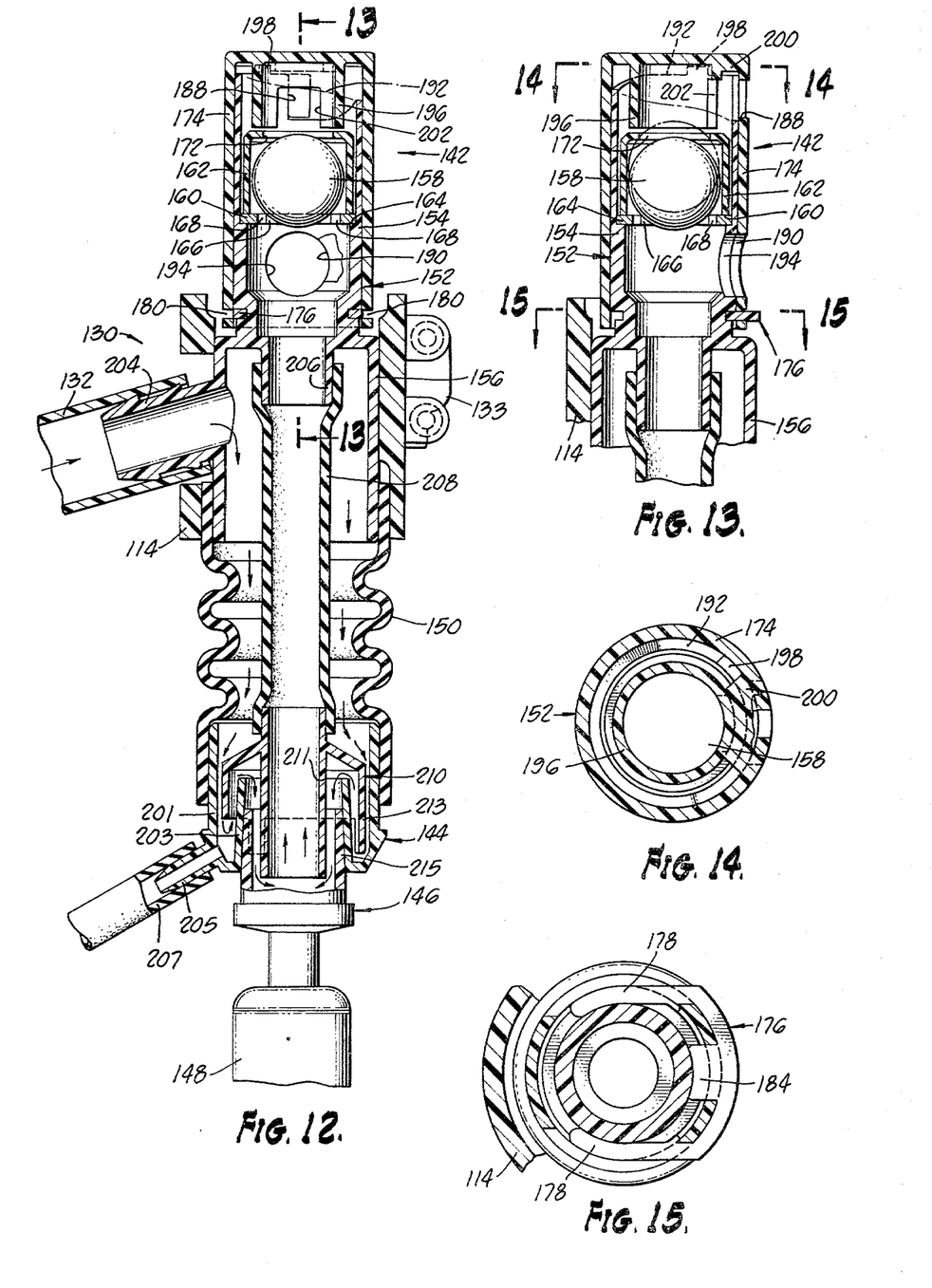
FIG. 12 is a sectional elevation view taken along the plane 12—12 of FIG. 2 and looking in the direction of the arrows, showing the vertical arm of the disposable airway set of the CPAP administration apparatus of the present invention.
FIG. 13 is a sectional elevation view taken along the plane 13—13 of FIG. 12 and looking in the direction of the arrows, showing the pressure control valve which forms the upper part of the vertical arm of the disposable airway set in the apparatus of the present invention.
FIG. 14 is a sectional plan view taken along the plane 14—14 of FIG. 13 and looking in the direction of the arrows, showing the inter-relationship of the top of the control valve cap and the upper end of the valve body in the pressure control valve.
FIG. 15 is a sectional plan view taken along the plane 15—15 of the FIG. 13 and looking in the direction of the arrows, showing the manner in which the valve cap and the valve body of the pressure control valve are attached to one another.

The vertical arm 130 of the disposable airway set 22, best shown in FIGS. 1, 3 and 13, includes a pressure control valve assembly 142 at the upper end thereof. An adapter 144, a connector 146, and a nasal cannula 148 are provided at the lower end of the vertical arm 130 of the disposable airway set 22. A corrugated tube 150 connects the lower end of the pressure control valve assembly 142 to the adapter 144.

The details of the structure of the vertical arm 130 of the disposable airway set 22 are best illustrated in FIG. 12. The pressure control valve assembly 142 includes a control valve body 152 having an upper section 154 and a lower section 156. The upper section 154 of the valve body 152 serves as housing for a ball check valve 158, a ball seat 160 and a ball retainer cage 162. The upper section 154 of the valve body 152 is generally cylindrical and includes an annular ledge 164 in the interior peripheral wall thereof on which the ball seat 160 is disposed. The ball seat 160 has a central opening 166 therein which is smaller in diameter than the ball check valve 158. A plurality of semi-circular openings 168 are provided around the periphery of the central opening 166 so that air may pass upwardly and around the ball 158 when the ball is seated on the ball seat 160. The ball retainer cage 162 is generally cup-shaped and has a central opening 172 in the upper end wall thereof. The ball retainer cage 162 fits over the ball 158 and rests on the ball seat 160.

A control valve cap 174 covers the upper section 154 of the control valve body 152 and is rotatably secured thereon by means of a generally E-shaped retaining clip 176 (best shown in FIGS. 12, 13 and 15). The generally E-shaped retaining clip 176 includes inwardly curved arms 178, 178 which extend through a pair of parallel side slots 180, 180 in the lower end of the cap 174 and an annular groove in the central portion of the valve body 152, between the upper and lower sections 154 and 156 thereof. As best shown in FIG. 15, the inwardly curved portions of the outer arms 178, 178 of the E-shaped retaining clip 176 grasp the central portion of the valve body 152, and a central, radially inwardly extending stub 184 on the E-shaped retaining clip extends through a central slot in the lower end of the cap 174 and through the annular groove in the central portion of the valve body 152. Thus, the central stub 184 and the inwardly curved arms 178, 178 of the E-shaped retaining clip 176 hold the cap 174 on the upper section 154 of the valve body 152 by spring force. As will be appreciated from viewing FIG. 15, if it is desired to remove the cap 174 from the upper section 154 of the control valve body 152, the E-shaped retaining clip 176 is simply pulled radially outwardly (to the right, as viewed in FIG. 15), whereupon the inwardly curved outer arms 178, 178 of the retaining clip 176 will be cammed radially outwardly to permit the clip to be pulled off.

The E-shaped retaining clip 176 holds the valve cap 174 on the upper section 154 of the valve body 152, while permitting the valve cap to be rotated relative to the valve body.

As shown in FIGS. 12 and 13, a rectangular opening 188 is provided in the wall of the valve cap 174 adjacent the upper end thereof, and a circular opening 190 is provided in the lower portion of the valve cap. The rectangular opening 188 is considerably smaller than the area of the circular opening 190.

The upper end of the upper section 154 of the valve body 152 is formed to provide a helical ramp 192 so that as the valve cap 174 is rotated on the upper section 154 of the valve body 152 the helical ramp 192 will cover all, a portion or none of the rectangular opening 188 in the upper end of the cap. Thus, the cap 174 may be rotated to any desired position so that the rectangular opening 188 therein may be wholly occluded, partially occluded (FIG. 12 position) or left entirely open (FIG. 13 position).

As shown in FIGS. 12 and 13, a circular opening 194 is provided in the upper section 154 of the valve body 152 which is the same size as the circular opening 190 in the valve cap. In FIG. 13, the circular openings 194 and 190 in the valve body 152 and the cap 174, respectively, are aligned with one another so that the interior of the valve body 152 is open to the atmosphere through the aligned circular openings 194 and 190.

A cylindrical boss 196 (FIGS. 12 and 13) is integrally formed on the end wall of the valve cap 174 and extends inwardly therefrom to a point adjacent the cup-shaped ball retainer cage 162. When air is forced upwardly through the upper section 154 of the valve body 152 under relatively high pressure, the ball check valve 158 will rise, and the ball retainer cage 162 will also rise. The ball check valve 158 and the ball retainer cage 162 will be stopped by the cylindrical boss 196. Thus the cylindrical boss 196 functions to limit upward movement of the ball retainer cage 162 off the ball seat 160.

As shown in FIGS. 12–14, an upwardly projecting stop 198 is provided on the highest portion of the helical ramp 192 on the upper section 154 of the valve body 152 for cooperating with an arcuate stop 200 (FIG. 14) provided between the cylindrical boss 196 and the outer wall at the upper end of the valve cap 174 for limiting rotational movement of the valve cap 174, relative to the upper section 154 of the valve body 152, to approximately 270°.

A cutaway portion 202 is provided in the wall of the cylindrical boss 196 (FIG. 12) to facilitate the passage of air through the rectangular opening 188 in the upper end of the valve cap 174.

The lower section 156 of the pressure control valve body is provided with a radially outwardly projecting nozzle 204 which is attached to one end of the connector hose 132 for receiving fresh air to be delivered to the patient (see FIG. 12).

As shown in FIG. 12, the upper end of the lower section 156 of the valve body 152 has a downwardly projecting circular stub 206 having one end of an exhaust tube 208 secured thereon. The other end of the exhaust tube is secured around the upper end of an exhaust-moisture deflector fitting 210 which is disposed in the adapter 144.

The lower end of the lower section 156 of the control valve body 152 is connected to the upper end of the adapter 144 by means of the corrugated tube 150.

One of the significant advantages of the present invention is realized by virtue of the construction of the lower end of the vertical arm 130 of the disposable airway set 22 which includes the exhaust-moisture deflector fitting 210, the adapter 144 and the connector 146.

As shown in FIG. 12, the nasal adapter 144 comprises an outer cylindrical wall 201 and an inner cylindrical wall 203 spaced radially inwardly therefrom. A downwardly and radially outwardly extending drain nozzle 205 is connected to the bottom end of the adapter 144 for draining water, which is collected from the incoming air by the exhaust-moisture deflector fitting 210. A drain tube 207 is connected to the nozzle 205 for carrying the collected water away.

The exhaust-moisture deflector fitting 210 includes a central exhaust tube 211 and a peripheral moisture deflector skirt 213 spaced radially outwardly therefrom. The peripheral moisture deflector skirt 213 extends into the annular chamber defined between the inner and outer cylindrical walls 203 and 201 of the adapter 144, and the inner cylindrical wall of the adapter extends into the annular chamber formed between the central exhaust tube 211 and the moisture deflector skirt 213 of the exhaust-moisture deflector fitting 210.

The connector 146 includes an upwardly extending tubular portion 215 which extends into the inner cylindrical wall 203 of the adapter 144 and is held therein by a friction fit. As shown in FIG. 12, the upper end of the upwardly extending tubular portion 215 of the connector 146 encloses the lower end of the central exhaust tube 211 of the exhaust-moisture deflector fitting 210.

By virtue of the construction and interrelationship of the adapter 144, the exhaust-moisture deflector fitting 210 and the connector 146, two phenomena occur: (1) the incoming fresh air follows a tortuous path, as shown by the arrows in FIG. 12, and (2) the amount of "dead air space" (i.e., the space in which air exhausted by the patient collects and could be rebreathed by the patient) is reduced to a minimum. The turbulance of the incoming air promotes better mixing of the incoming air with the air exhausted by the patient to carry the exhausted air away, through the exhaust tube 208 and the pressure control valve 142. The reduction of "dead air space" minimizes the amount of exhausted air which would otherwise be rebreathed by the patient.

It is contemplated that a conventional endotracheal tube (not shown) rather than the nasal cannula 148 may be connected to the connector member 146, if desired.

Referring to FIG. 1, fresh air, under pressure, is delivered to the cross-connector tube 138 in the horizontal arm 128 of the disposable airway set 22. The pop-off valve assembly 134 functions to limit the pressure of the fresh air delivered to the patient, while permitting periodic "bursts" of fresh air to be delivered to the patient when the rebreather bag 136 is squeezed. This delivery of periodic "bursts" of fresh air to the patient is called "bagging".

Referring to FIG. 9, the pop-off valve assembly 134 includes a housing 220 for a gate valve 222. The upper end of the housing 220 is covered by a cover member 224 having a central opening 226 therein. The central opening 226 is normally closed by means of a diaphragm 228 which is disposed in a generally cylindrical cap member 230 having circumferentially-spaced openings 232 therein. A compression spring 234 is disposed in the cap member 230 between the upper end thereof and the diaphragm 228. The upper end of the compression spring 234 is confined in a cylindrical housing 236 in the cap member 230, and the lower end of the compression spring 234 fits around an upwardly projecting cylindrical boss 238 on the diaphragm 288.

Under normal conditions, i.e., when the pressure of the incoming fresh air is below a predetermined maximum, the compression spring 234 maintains the diaphragm 228 in the closed position shown in FIG. 9, so that none of the fresh air will pass out of the horizontal arm 128 of the disposable airway set 22, and all of the fresh air can be delivered to the patient through the connector tube 132 (FIG. 1) and the vertical arm 130 of the disposable airway set (FIG. 12).

If the pressure of the incoming fresh air exceeds a predetermined maximum, the pressure will lift the diaphragm 228 off of the cover member 224 (FIG. 9), against the force of the compression spring 234 so that some of the incoming air will pass out of the system through the central opening 226 in the cover member 224 and the openings 232 in the cap member 230.

The gate valve 222 provided in the gate valve housing 220 closes the pop-off valve assembly when it is desired to "bag" the patient by squeezing the rebreather bag 136. The gate valve 222 is pivotably connected to a downwardly extending projection 240 on the cover member 224 which covers the gate valve housing 220. The lower wall 242 of the gate valve housing is shaped in the form of a right angle so that the gate valve 222 normally rests in the position shown in FIG. 9.

When it is desired to "bag" the patient, the rebreather bag 136 is squeezed periodically by the attending physician or other hospital personnel. The air forced out of the rebreather bag 136 will cause the gate valve 222 to pivot in a clockwise direction, as viewed in FIG. 9, to close the opening 226 in the cover member 224 covering the gate valve housing 220. This will permit delivery of "bursts" of fresh air to the patient.

SET-UP FOR OPERATION OF THE PREFERRED EMBODIMENT OF THE CPAP ADMINISTRATION APPARATUS OF THE PRESENT INVENTION

To set up the preferred embodiment of the continuous positive airway pressure administration shown in the drawings and described above, the cradle assembly 26 is first assembled, the support frame assembly 24 is assembled and mounted on the cradle and positioned in the desired place, and the disposable airway set 22 is inserted into the support frame assembly 24.

To assemble the cradle assembly 26, the cradle release lever 38 is pulled rearwardly (i.e., to the left as viewed in FIGS. 1A and 2) and the end of the cradle 34 without the track 74 thereon is inserted into the arcuate groove 32 in the base member 30, beneath the inwardly extending ledges 35, 35 on the base member. Thereafter, the cradle 34 is rotated to the desired angular position and the cradle release lever 38 is released so that the spring-loaded pin 40 extends into one of the slots 36 in the side of the cradle 34. It should be noted that the cradle 34 should be inserted into the arcuate groove 32 in the base member 30 from the desired direction (i.e., from the right or left, as viewed in FIG. 3) so that the track 74 on one end of the cradle 34 will be on the desired side of the patient so that the support frame assembly 24, when mounted on the track 74, and the disposable airway set 22 which is inserted into the support frame assembly 24 will all be on the desired side (i.e., the left or right) of the patient when the apparatus 20 is fully assembled.

After the cradle 34 has been positioned in the arcuate groove 32 of the base 30, the pad 56 is positioned to cover the inside of the cradle 34 by placing the pockets 58, 58 onto the upper end of the head restraining plates 54, 54.

After the cradle assembly 26 has been assembled, the support frame assembly 24 is mounted on the end of the cradle 34 which has the track 74 thereon by sliding the clamping member 92 having the track groove 100 therein onto the track 74 as shown in FIG. 3. When the support frame assembly 24 is laterally positioned on the track 74, the locking bolt 96 and the adjustment screw 86 are tightened so that the track 74 will be firmly grasped between the two clamping members 92 and 94.

With the support frame assembly positioned and clamped on the track 74, the horizontal portion 112 of the support arm 80 is inserted into the cylindrical holder 76 of the support frame assembly 24 until the circumferential shoulder 126 on the rear section of the horizontal portion 112 of the support arm 80 abuts the rear end of the cylindrical holder 76 (see FIG. 9). It will be noted that as the forward section 118 of the horizontal portion 112 of the support arm 80 is being inserted into the cylindrical holder 76 of the support frame assembly 24, the horizontally extending portion 112 of the support arm 80 must be angularly positioned so that the radially outwardly extending key member 119 on the forward section 118 will slide in the horizontal slot 122 in the cylindrical holder 76 (see FIGS. 9 and 11).

With the support arm 80 inserted in the support frame assembly 24, the support arm 80 is in position to receive a disposable airway set 22.

A disposable airway set 22 is simply positioned in the support arm 80 by sliding the forward end of the crossconnector tube 138 of the disposable airway set 22 into the horizontally extending portion 112 of the support arm 80 (see FIG. 9) and positioning the lower section 156 of the control valve body 152 in the vertically extending portion 114 of the support arm 80 and pivoting the gate 133 to its closed position shown in FIG. 3. As the lower section 156 of the control valve body 152 is being positioned in the vertically extending portion 114 of the support arm 80, the connecting hose 132 between the horizontal arm 128 and the vertical arm 130 of the disposable airway set 22 is positioned in the semi-cylindrical connecting portion 116 of the support arm 80, as shown in FIG. 3.

With the cradle assembly 26, the support frame assembly 24, the support arm 80 and the disposable airway set 22 assembled in the manner set forth above, the continuous positive airway pressure administration apparatus 20 of the present invention is now in condition to receive a patient to whom continuous positive airway pressure is to be delivered.

OPERATION OF PREFERRED EMBODIMENT OF CPAP ADMINISTRATION APPARATUS OF THE PRESENT INVENTION

A patient (e.g., an infant) to whom continuous positive airway pressure is to be delivered, is positioned with his head between the restraining plates 54, 54 in the cradle assembly 26. The adjustment knobs 66, 66 are then loosened and slid downwardly to urge the slide members 68, 68 against the ramps 62, 62 on the outer surfaces of the head restraining plates 54, 54 to cam the head restraining plates 54, 54 inwardly. When the head restraining plates 54, 54 have been moved inwardly to closely conform to the patient's head, the adjustment knobs 66, 66 are tightened to lock the head restraining plates 54, 54 in place. The pad 56 which covers the head restraining plates 54, 54 will cushion the patient's head and prevent the head restraining plates 54, 54 from injuring or causing discomfort to the patient's head.

While the head of the patient is being inserted in place in the cradle assembly 26, the support arm 80 and the disposable airway set 22 are moved to the position shown in phantom lines in FIG. 3, out of the way of the patient's head. As noted above, the radially outwardly extending key member 119 on the horizontally extending portion 112 of the support arm 80 which rides in the arcuate slot 120 in the cylindrical holder 76 of the cradle assembly 26 permits the support arm 80 and the disposable airway set 22 between the "down" position shown in solid lines in FIG. 3 and the "up" position shown in phantom lines in FIG. 3.

With the head of the patient firmly supported in the cradle assembly 26, the support arm 80 and the disposable airway set 22 carried thereby are pivoted to the "down" position shown in solid lines in FIG. 3. The two downwardly extending mostril inserts 244, 244 on the nasal cannula 148 (FIG. 3) are then positioned in the nostrils of the patient and the disposable airway set 22 is connected to a source of fresh air, under pressure, by connecting the forward end of the cross-connector tube 138 (FIG. 9) to the air supply hose 140.

Fresh air under pressure will then be delivered through the cross-connector tube 138 (FIG. 9), and the connecting hose 132 of the disposable airway set 22 (FIG. 22) to the nozzle 204 (FIG. 12) on the lower section 156 of the pressure control valve body 152.

As shown by arrows in FIG. 12, fresh air under pressure will be delivered through the nozzle 204 to the annular space between the lower section 156 of the control valve body and the upper portion of the exhaust tube 208. Fresh air will continue downwardly through the annular section between the corrugated tube 150 and the exhaust tube 208 and through the tortuous path defined by the adapter 144, the exhaust-moisture deflector fitting 210 and the connector 146, to the nasal cannula 148 and the patient.

As the fresh air being delivered to the patient follows the tortunous path to the patient, moisture in the air will collect on the moisture deflector skirt 213 of fitting 210 and will drip down into the lower annular space in the adapter 144. From this annular space, the moisture will drain through the drain nozzle 205 and drain tube 207 so that it will never reach the patient.

As the patient exhales, the carbon dioxide will pass upwardly through the central exhaust tube 211 of the fitting 210, the exhaust tube 208 and the pressure control valve assembly 142 to the atmosphere. The carbon dioxide being exhaled by the patient will pass through the circular opening 194 in the upper section 154 of the control valve body and the circular opening 190 in the valve cap 174, to the atmosphere. Carbon dioxide will also be exhaled through the semi-circular openings 168 in the ball seat 160 and will pass around the ball check valve 158 and through the rectangular opening 188 in the valve cap 174.

By virtue of the construction and interrelationship of the adapter 144, the exhaust-moisture deflector fitting 210 and the connector 146 at the lower end of the vertical arm 130 of the disposable airway set 22, the "dead air space" is reduced to a minimum and the incoming fresh air follows a tortuous path. As a result, a maximum of fresh air is delivered to the patient and only a minimal amount of exhausted air is rebreathed.

The pressure of the fresh air being delivered to the patient may be controlled by rotating the control valve cap 174 on the upper section 154 of the control valve body 152 (FIG. 12) to occlude or partially occlude the circular opening 194 in the upper section 154 of the control valve body 152 and/or the rectangular opening 188 in the valve cap 174.

Referring to FIG. 9, it will be noted that the popoff valve assembly 134 in the horizontal arm 128 of the disposable airway set 22 will function to limit the maximum pressure of the fresh air being delivered to the patient. If the pressure of the fresh air passing through the cross-connector tube 138 becomes greater than a predetermined maximum, it will lift the diaphragm 228 off of its seat on the cover member 224, against the force of the compression spring 234, to vent the excessive pressure to the atmosphere through the openings 232 in the cap member 230.

When it is desired to "bag" the patient, the rebreather bag 136 is squeezed by the attending physician or other hospital personnel to force "bursts" of fresh air into the patient. As the rebreather bag 136 is squeezed, the gate valve 222 will be forced, by air pressure, upwardly, to close the central opening 226 in the cover member 224 of the pop-off valve assembly.

It will be noted that the lateral position of the support arm 80 and the disposable airway set 22 carried thereby can be changed at any time by simply lossening the adjustment screw 86 and sliding the entire support frame assembly along the track 74 (FIG. 3) until the support frame assembly 28 and the support arm 80 and the disposable airway set 22 carried thereby are in the desired lateral position.

The disposable airway set 22 of the apparatus 20 of the present invention is designed to be discarded after each use. The disposable airway set 22 may be removed from the support arm 80 of the support frame assembly 24 by simply lifting the gate 133 (FIG. 1) and pulling the disposable airway set out (i.e., to the right, as viewed in FIG. 1). A new, sterilized disposable airway set 22 may then be inserted into the support arm 80 of the support frame assembly 24 for delivering continuous positive airway pressure to the next patient.

From the foregoing, it will be appreciated that the present invention provides a convenient, adjustable, sturdy, relatively inexpensive continuous positive airway pressure administration apparatus which includes a sterile disposable airway set which may be discarded after each use. The employment of a disposable airway set insures that each patient will have a completely sterilized airway set. Yet, since the airway set is disposable, it will not be necessary for the hospital to carry out the relatively expensive and time consuming sterilization procedures that have been necessary when employing the continuous positive airway pressure administration apparatus of the prior art.

It will also be appreciated from the foregoing that the disposable airway set of the apparatus of the present invention provides numerous desirable features to insure that continuous positive airway pressure is delivered to each patient in a safe, reliable and effective manner.

It is contemplated that numerous modifications may be made to the continuous positive airway pressure administration apparatus of the present invention without departing from the spirit and scope of the invention. Accordingly, it is intended that the scope of this patent be limited only by the scope of the appended claims.

What we claim is:

1. In a system for administering gas at an elevated pressure to a patient requiring respiratory support, the improvement comprising:
   generally annular inner wall means defining a central fluid exhaust passage;
   said inner wall means including a distal end portion adapted to be disposed adjacent to a patient's breathing passage;
   means establishing fluid communication between said central fluid exhaust passage and the atmosphere for carrying gas exhaled by a patient away from said system;
   generally annular outer wall means spaced from and extending around said inner wall means to define a generally annular fluid delivery passage between said inner and outer wall means;

said outer wall means including a distal end portion spaced radially-outwardly from said distal end portion of said inner wall means;

means for establishing fluid communication between said fluid delivery passage and a source of gas under pressure to be delivered to a patient; and inner intermediate wall member and an outer intermediate wall member disposed between said distal end portions of said inner and outer wall means and cooperating therewith to define a tortuous flow path for gas to be delivered to a patent;

said inner intermediate wall member being disposed between said distal end portion of said inner wall means and said outer intermediate wall member;

said outer intermediate wall member being disposed between said inner intermediate wall member and said distal end portion of said outer wall means;

each of said inner and outer intermediate wall members including a distal end portion and a proximal end portion;

a generally annular proximal wall means connecting said proximal end portion of said outer intermediate wall member to said inner wall means;

a generally annular distal wall means connecting said distal end portion of said inner intermediate wall member to said outer wall means;

said proximal end portion of said inner intermediate wall member being spaced from said generally annular proximal wall means;

said distal end portion of said outer intermediate wall member being spaced from said generally annular distal wall means;

means defining a drain port in said distal wall means for draining condensate collected in the annular space between the distal end portions of said outer wall means and said inner intermediate wall member;

said central fluid exhaust passage and said generally annular fluid delivery passage including distal end portions adjacent said distal end portions of said inner and outer wall means; and means for connecting said distal end portions of said central fluid exhaust passage and said generally annular fluid delivery passage in fluid communication with a breathing passage of a patient.

2. In a system for administering gas at an elevated pressure to a patient requiring respiratory support, the improvement comprising:

generally annular inner wall means defining a central passage;

said inner wall means including a distal end portion adapted to be disposed adjacent to a patient's breathing passage;

generally annular outer wall means spaced from and extending around said inner wall means to define a generally annular passage between said inner and outer wall means;

said outer wall means including a distal end portion spaced radially-outwardly from said distal end portion of said inner wall means;

means establishing fluid communication between one of said passages and the atmosphere for carrying gas exhaled by a patient away from said system;

means for establishing fluid communication between the other of said passages and a source of gas under pressure to be delivered to a patient;

an inner intermediate wall member and an outer intermediate wall member disposed between said distal end portions of said inner and outer wall means and cooperating therewith to define a tortuous flow path for gas to be delivered to a patient;

said inner intermediate wall member being disposed between said distal end portion of said inner wall means and said outer intermediate wall member;

said outer intermediate wall member being disposed between said inner intermediate wall member and said distal end portion of said outer wall means;

each of said inner and outer intermediate wall members including a distal end portion and a proximal end portion;

a generally annular proximal wall means connecting said proximal end portion of said outer intermediate wall member to said inner wall means;

a generally annular distal wall means connecting said distal end portion of said inner intermediate wall member to said outer wall means;

said proximal end portion of said inner intermediate wall member being spaced from said generally annular proximal wall means;

said distal end portion of said outer intermediate wall member being spaced from said generally annular distal wall means; and means defining a drain port in said distal wall means for draining condensate collected in the annular space between the distal end portions of said outer wall means and said inner intermediate wall member.

3. A system for administering gas at an elevated pressure to a patient requiring respiratory support, comprising:

generally tubular inner wall means defining a central exhaust passage;

said inner wall means including a distal end portion adapted to be disposed adjacent to a patient's breathing passage;

means establishing fluid communication between said central exhaust passage and the atmosphere for carrying gases exhaled by a patient away from said system;

generally tubular outer wall means extending around said inner wall means; said inner and outer wall means defining an annular delivery passage therebetween;

said outer wall means including a distal end portion spaced radially-outwardly from said distal end portion of said inner wall means;

means for connecting said annular delivery passage to a source of gas under pressure;

baffle means disposed between said distal end portions of said inner and outer wall means; said baffle means cooperating with said inner and outer wall means to define a tortuous flow path for gas delivered to a patient via said annular delivery passage;

said baffle means comprising an inner intermediate wall member and an outer intermediate wall member; said inner intermediate wall member being disposed between said distal end portion of said inner wall means and said outer intermediate wall member; and said outer intermediate wall member being disposed between said inner intermediate wall member and said distal end portion of said outer wall means;

drain means between said distal end portions of said inner and outer wall means for draining condensate from gas delivered to a patient; and means for connecting said distal end portions of said annular delivery passage and said central exhaust passage in fluid communication with a breathing passage of a patient.

4. A system according to claim 3, wherein each of said inner and outer intermediate wall members includes a distal end portion and a proximal end portion; and further comprising a generally annular proximal wall means connecting said proximal end portion of said outer intermediate wall member to said inner wall means, and a generally annular distal wall means connecting said distal end portion of said inner intermediate wall member to said outer wall means; said proximal end portion of said inner intermediate wall member being spaced from said generally annular proximal wall means; and said distal end portion of said outer intermediate wall member being spaced from said generally annular distal wall means.

5. A System according to claim 4, and further comprising means defining a drain port in said distal wall means for draining condensate collected in the annular space between the distal end portions of said outer wall means and said inner intermediate wall member.

6. A system according to claim 3, and further comprising wall means extending between said inner intermediate wall member and said outer wall means to define a collection area for collecting condensate from gas delivered to a patient.

7. A system for administering gas at an elevated pressure to a patient requiring respiratory support, comprising:

generally tubular inner wall means defining a central passage;

generally tubular outer wall means extending around said inner wall means; said inner and outer wall means defining an annular passage therebetween;

means establishing fluid communication between one of said passages and the atmosphere for carrying gases exhaled by a patient away from said system;

means for connecting the other of said passages to a source of gas under pressure;

said central passage and said annular passage and each of said inner and outer wall means including a distal end portion adapted to be disposed adjacent to a patient's breathing passage;

means for connecting said distal end portions of said central passage and said annular passage in fluid communication with a breathing passage of a patient;

baffle means disposed between said distal end portions of said inner and outer wall means; said baffle means cooperating with said inner and outer wall means to define a tortuous flow path for gas delivered to a patient;

said baffle means comprising an inner intermediate wall member and an outer intermediate wall member; said inner intermediate wall member being disposed between said distal end portion of said inner wall means and said outer intermediate wall member; and said outer intermediate wall member being disposed between said inner intermediate wall member and said distal end portion of said outer wall means; and drain means between said distal end portions of said inner and outer wall means for draining condensate from gas delivered to a patient.

8. A system according to claim 7, wherein each of said inner and outer intermediate wall members includes a distal end portion and a proximal end portion; and further comprising a generally annular proximal wall means connecting said proximal end portion of said outer intermediate wall member to said inner wall means, and a generally annular distal wall means connecting said distal end portion of said inner intermediate wall member to said outer wall means; said proximal end portion of said inner intermediate wall member being spaced from said generally annular proximal wall means; and said distal end portion of said outer intermediate wall member being spaced from said generally annular distal wall means.

9. A system according to claim 8, and further comprising means defining a drain port in said distal wall means for draining condensate collected in the annular space between the distal end portions of said outer wall means and said inner intermediate wall member.

10. A system according to claim 7, and further comprising wall means extending between said inner intermediate wall member and said outer wall means to define a collection area for collecting condensate from gas delivered to a patient.

* * * * *